United States Patent [19]

Hess et al.

[11] Patent Number: 5,084,553

[45] Date of Patent: Jan. 28, 1992

[54] COPOLYMERS OF LACTIC ACID AND TARTARIC ACID, THE PRODUCTION AND THE USE THEREOF

[75] Inventors: Joachim Hess, Bingen; Klaus R. Müller, Ingelheim am Rhein, both of Fed. Rep. of Germany

[73] Assignee: Boehringer Ingelheim KG, Ingelheim am Rhein, Fed. Rep. of Germany

[21] Appl. No.: 606,672

[22] Filed: Oct. 31, 1990

[30] Foreign Application Priority Data

Oct. 31, 1989 [DE] Fed. Rep. of Germany ....... 3936191

[51] Int. Cl.⁵ .................... C08G 63/06; C09D 167/04
[52] U.S. Cl. .................................... 528/361; 528/354
[58] Field of Search ................ 528/354, 361; 523/213; 525/27; 521/157, 99; 524/839; 430/546; 549/274

[56] References Cited

U.S. PATENT DOCUMENTS 4,000,111 12/1976 Henman et al. ...................... 523/213
4,983,745 1/1991 Muller et al. ......................... 549/274

Primary Examiner—John Kight, II
Assistant Examiner—Shelley A. Wright
Attorney, Agent, or Firm—D. E. Frankhouser; M-E. M. Timbers; A. R. Stempel

[57] ABSTRACT

The invention relates to new copolymers of lactic acid and tartaric acid, the preparation and use thereof.

15 Claims, No Drawings

COPOLYMERS OF LACTIC ACID AND TARTARIC ACID, THE PRODUCTION AND THE USE THEREOF

The invention relates to new biodegradable copolymers of lactic acid and tartaric acid, the production and use thereof.

For the purposes of the present invention, unless otherwise stated, the term biodegradable or resorbable means that the polymer will dissolve and be broken down into toxicologically harmless products in the course of time under the physiological conditions which prevail in the human or animal body.

In recent years, considerable attention has been given to the development of biodegradable copolymers which contain lactic acid units. The particular importance of lactic acid, especially in connection with the use of copolymers which contain lactic acid for medical purposes, is based on the good physiological acceptability which characterises lactic acid.

Whereas lactic acid or lactide have been cocondensed or copolymerised with a plurality of different monomers, in the course of the development of biodegradable copolymers of this kind for all kinds of applications, copolymers containing lactic acid and tartaric acid units have hitherto been unknown.

The term "lactic acid", as used in the present application, includes D-lactic acid and L-lactic acid and mixtures thereof. Similarly, the word tartaric acid (dihydroxysuccinic acid) includes the two enantiomers (+)-tartaric acid [(2R, 3R)-(+)-tartaric acid] and (−)-tartaric acid [(2S, 3S)-(−)-tartaric acid] and the racemate (racemic acid) and the optically inactive mesotartaric acid and mixtures thereof.

Whereas it is generally only possible to produce unbranched linear polyesters by the polycondensation of lactic acid with the α-hydroxycarboxylic acids conventionally used, the cocondensation of lactic acid and tartaric acid results in cocondensation products having branched structures.

Polycocondensates based on lactic acid, which have a linear structure, have relatively low molecular weights. Thus, copolymers of lactic acid and glycolic acid have a molecular weight which does not exceed 3500 to 4000, which is reflected in the values for the inherent viscosity, which are in the range from about 0.1 to 0.15 dl/g. By contrast, the polycondensation products of lactic acid and tartaric acid according to the invention have inherent viscosities of more than 0.5 dl/g, even though the polycondensation takes only a fraction of the time needed for the polycondensation of lactic acid and glycolic acid.

The copolymers according to the invention are synthesized essentially from units of formula I

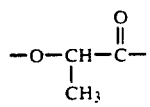

and units of formula II

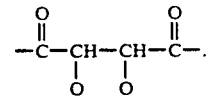

Depending on the particular extent of reaction, free carboxyl or hydroxyl groups may be present in both units in smaller or larger amounts.

In the polycondensation products according to the invention, the ratio of lactic acid units to tartaric acid units is in the range from 1:2 to 60:1. A range from 1:1 to 50:1 is preferred, whilst the range from 5:1 to 30:1 is particularly preferred.

The copolymers according to the invention have inherent viscosity values (measured in 0.1% solution in acetone at 20° C.) in the range from 0.2 to 1 dl/g, preferably 0.2 to 0.8 dl/g. Copolymers with an inherent viscosity in the range from 0.2 to 0.6 dl/g are particularly preferred.

Moreover, the cocondensates according to the invention may contain smaller amounts of units of another hydroxycarboxylic acid or additional monomers selected from the group comprising the lactones or lactides may also be introduced into the condensation reaction.

The products according to the invention are insoluble in the majority of common organic solvents or will swell up considerably in such solvents, indicating crosslinking in the polymer.

By comparison with the polymers known hitherto, the copolymers according to the invention contain a large proportion of free carboxyl groups. Consequently, it is possible to control their water solubility by means of the pH value.

The biodegradable polyesters according to the invention thus have novel physical and chemical properties which appear to render them suitable for a plurality of interesting applications, just a few of which are mentioned by way of example:

1) The polycondensation products according to the invention are suitable as carriers (matrix) or devices for storing therapeutic agents or as retardant excipients for use in drug release systems in which the active substance is supposed to be released in controlled manner. In drug release systems of this kind it is desirable for the polymer to dissolve during or after release of the drug, leaving no undesirable or pharmacologically harmful residues in the tissues.

In view of their pH-dependent solubility in water, the copolymers according to the invention are particularly useful for an application of this kind since this property opens up another possible way of influencing the release characteristics, in addition to the methods known from the art which have been available hitherto.

Methods of charging the polycondensation products according to the invention with an active substance or substances, or of constructing the drug release system, e.g. by specific measures, so as to achieve specific release characteristics are known from the prior art. The condensation products according to the invention have the additional advantage that the high number of free carboxyl groups present in the polymer make it possible for suitable active substances to bond to the matrix physically and/or chemically without the need for any further modifications to the polymer.

Release systems of this kind may be designed as an implant or for oral administration or for use in the form of an aerosol.

The absorbable polycondensation products may, for example, be ground and compressed with the required active substances and possibly other excipients, e.g. binders or flavourings, to form tablets or they may be processed to produce coated tablets or pellets. The methods used are known from the prior art. In this application, also, the pH-dependent water solubility of the copolymer according to the invention constitutes a particular advantage since targeted release can be achieved, in view of the fact that the stomach is an acidic medium whereas the intestines are an alkaline medium.

2) The copolymers according to the invention are also suitable for use in the form of resorbable and surgical aids used in surgical interventions.

The particular applications of such polymers are known from the prior art. Generally speaking, these possible uses are determined primarily by the mechanical properties, on the one hand, and by the degradation characteristics in vivo, on the other hand. Both characteristics can be controlled over a wide range, inter alia, by the composition of the particular cocondensation products used.

The use of resorbable polymers have always proved particularly advantageous when removal of the surgical fixing device (e.g. clips, orthopedic pins or splints) after the operation has ended would involve considerable work or an element of risk, e.g. owing to difficulty of access.

However, even in the opposite situation, i.e. when there is always the intention to remove the surgical aid at the end of the intervention, the use of the polycondensation products according to the invention proves advantageous, since the biodegradable polymers, unlike the non-degradable ones, can usually be absorbed by the body without any harmful consequences if they should accidentally be left in the body, and will not result in any complications. Examples include plastic implants, dental packings or haemostatic devices. If necessary, the surgical aids prepared from the cocondensation products according to the invention may also be used as carriers for drugs, such as anti-inflammatory or bactericidal agents, or they may be charged with a substance which produces an X-ray contrast.

3) The controllable water-solubility of the cocondensates according to the invention as described above also makes it possible for them to be used, for example, as carriers or containers for agrochemicals, herbicides or insecticides, for example. The relatively high content of free carboxyl groups also has the advantage, in this application, that larger quantities of active substance can be chemically and/or physically bound to the matrix, compared with the therapeutic preparations.

4) In another application, the polycondensation products according to the invention may be designed, by increasing the proportion of tartaric acid, so that they dissolve extremely easily in water. This property renders them suitable for use in the form of protective films or foils which can easily be removed without the use of other organic or inorganic solvents. The use of the polycondensates according to the invention has the major advantage that the polymerisation product itself as well as the hydrolysis products thereof are biodegradable, ensuring that they are environmentally very acceptable.

The polymers according to the invention may be prepared by the methods of polycondensation known from the prior art, optionally in the presence of a condensation catalyst. Instead of lactic acid or the enantiomers thereof, the corresponding lactides may also be used as starting material. The addition of another hydroxycarboxylic acid, a lactone or lactide may take place before or during the reaction. The Examples which follow are intended to illustrate the invention without restricting it.

EXAMPLE 1

500 g of L-lactic acid (90% = 5.0 mol) are mixed with 150.1 g of L-tartaric acid (1.0 mol) in a stirring apparatus consisting of a 1 liter sulphating flask with stirrer, thermometer and reflux condenser designed as a dephlegmator (80° C.). The reaction mixture is slowly heated to about 170° C., with stirring and under reduced pressure (water jet vacuum), whilst the water of reaction formed is distilled off through the dephlegmator. The reaction of polycondensation is continued until the viscosity of the colourless molten product produced increases to such a level that it is extremely difficult to mix the product with the stirrer.

After the reaction product has been taken out, the physical and chemical data shown in Table 1 for the compositions of lactic acid and tartaric acid indicated therein are determined:

| Example No. | Ratio LA/TA[1] | Reaction time/h | Inh. visc. dl/g | Acid content/% COOH[2] |
|---|---|---|---|---|
| 1 | 5/1 | 5.7 | 0.20 | 12.0–13.0 |
| 2 | 10/1 | 12.5 | 0.54 | 7.5–8.0 |
| 3 | 20/1 | 25.5 | 0.53 | 5.8 |
| 4 | 30/1 | 39.0 | 0.41 | 4.3 |

[1] LA: L-lactic acid TA: L-tartaric acid
[2] % by weight

What is claimed is:

1. A copolymer comprising units of formula I

and units of formula II

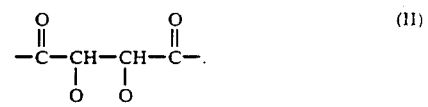

2. The copolymer as recited in claim 1 further characterised in that the ratio of lactic to tartaric acid units is in the range from about 1:2 to about 60:1.

3. The copolymer as recited in claim 1 further characterised in that the ratio of lactic to tartaric acid units is in the range from about 1:1 to about 50:1.

4. The copolymer as recited in claim 1 further characterised in that the ratio of lactic to tartaric acid units is in the range from about 5:1 to about 30:1.

5. The copolymer as recited in claim 1 further characterised in that it has an acid content of more than about 4.3% of free carboxyl groups.

6. The copolymer as recited in claim 1 further characterised in that it has values for inherent viscosity in the range from about 0.2 to about 1 dl/g, measured in approximately 0.1% solution in acetone at about 20° C. C.

7. The copolymer as recited in claim 6 further characterised in that it has values for inherent viscosity in the range from about 0.2 to about 0.8 dl/g, measured in approximately 0.1% solution in acetone at about 20° C.

8. The copolymer as recited in claim 6 further characterised in that it has values for inherent viscosity in the range from about 0.2 to about 0.6 dl/g, measured in approximately 0.1% solution in acetone at about 20° C.

9. The copolymer as recited in claim 1 further characterized in that the ratio of lactic to tartaric acid units is in the range from about 1:2 to about 60:1.

10. The copolymer as recited in claim 1 further characterised in that the ratio of lactic to tartaric acid units is in the range from about 1:1 to about 50:1.

11. The copolymer as recited in claim 1 further characterised in that the ratio of lactic to tartaric acid units is in the range from about 5:1 to about 30:1.

12. The copolymer as recited in claim 1 further characterized in that it has an acid content of more than about 4.3% of free carboxyl groups.

13. The copolymer as recited in claim 1 further characterised in that it has values for inherent viscosity in the range from about 0.2 to about 1 dl/g, measured in approximately 0.1% solution in acetone at about 20° C.

14. The copolymer as recited in claim 13 further characterised in that it has values for inherent viscosity in the range from about 0.2 to about 0.8 dl/g, measured in approximately 0.1% solution in acetone at about 20° C.

15. The copolymer as recited in claim 13 further characterised in that it has values for inherent viscosity in the range from about 0.2 to about 0.6 dl/g, measured in approximately 0.1% solution in acetone at about 20° C.

* * * * *